(12) United States Patent
Kato et al.

(10) Patent No.: US 9,297,741 B2
(45) Date of Patent: *Mar. 29, 2016

(54) CORROSION DETECTION SENSOR DEVICE

(71) Applicant: SEIKO EPSON CORPORATION, Tokyo (JP)

(72) Inventors: Juri Kato, Nagano (JP); Takao Miyazawa, Shimosuwa-machi (JP)

(73) Assignee: Seiko Epson Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/596,850

(22) Filed: Jan. 14, 2015

(65) Prior Publication Data

US 2015/0123683 A1    May 7, 2015

Related U.S. Application Data

(63) Continuation of application No. 13/426,938, filed on Mar. 22, 2012, now Pat. No. 8,937,476.

(30) Foreign Application Priority Data

Mar. 22, 2011 (JP) ................................ 2011-062764

(51) Int. Cl.
*G01N 17/02* (2006.01)
*G01N 33/20* (2006.01)
(Continued)

(52) U.S. Cl.
CPC .............. *G01N 17/02* (2013.01); *G01N 27/125* (2013.01); *G01N 27/4167* (2013.01); *G01N 31/221* (2013.01); *G01N 33/20* (2013.01); *G01N 33/383* (2013.01)

(58) Field of Classification Search
CPC . G01N 17/02; G01N 27/125; G01N 27/4167; G01N 27/048; G01N 33/383; G01N 33/20; G01N 17/04; G01N 17/006; G01N 31/221; G01N 33/38; G01N 21/80; G01N 2291/0258; G01N 27/02; G01N 29/2487; C23F 2201/02
See application file for complete search history.

(56) References Cited

U.S. PATENT DOCUMENTS

| 3,817,795 A | 6/1974 | Pourbaix |
| 4,433,093 A | 2/1984 | Shida et al. |

(Continued)

FOREIGN PATENT DOCUMENTS

| CN | 1945278 A | 4/2007 |
| JP | 09-171012 A | 6/1997 |

(Continued)

OTHER PUBLICATIONS

Hualan et al.; Principles of Structure Design; Published by Yellow River Water Conservancy Press on Aug. 31, 2008; pp. 15-24.

*Primary Examiner* — Vinh Nguyen
(74) *Attorney, Agent, or Firm* — Global IP Counselors, LLP

(57) ABSTRACT

A sensor device includes first and second electrodes, a coating film and a functional element. The first electrode includes a first metallic material in which either a first passivation film forms on a surface thereof or the first passivation film present on the surface thereof is lost, in association with changes in the pH of a measurement site. The second electrode includes a second metallic material different from the first metallic material, and is spaced apart from the first electrode. The coating film includes a third metallic material different from the first and second metallic materials. The coating film covers at least the first or second electrode. The functional element is configured to measure a difference in electric potential between the first and second electrodes that changes depending on presence or absence of each of the first passivation film and the coating film in association with the changes in pH.

21 Claims, 11 Drawing Sheets

(51) Int. Cl.
*G01N 27/416* (2006.01)
*G01N 27/12* (2006.01)
*G01N 31/22* (2006.01)
*G01N 33/38* (2006.01)

(56) References Cited

U.S. PATENT DOCUMENTS

| | | | |
|---|---|---|---|
| 4,940,945 A | 7/1990 | Littlejohn et al. | |
| 5,141,868 A | 8/1992 | Shanks et al. | |
| 5,320,735 A | 6/1994 | Kato et al. | |
| 5,483,164 A | 1/1996 | Moss et al. | |
| 5,609,740 A | 3/1997 | Hasegawa et al. | |
| 5,792,337 A | 8/1998 | Padovani et al. | |
| 6,015,484 A | 1/2000 | Martinchek et al. | |
| 6,549,015 B2 | 4/2003 | Horie et al. | |
| 6,773,563 B2 * | 8/2004 | Matsumoto | 204/401 |
| 6,796,187 B2 * | 9/2004 | Srinivasan et al. | 73/784 |
| 7,034,660 B2 | 4/2006 | Watters et al. | |
| 7,063,781 B2 | 6/2006 | Murray et al. | |
| 7,378,852 B2 | 5/2008 | Brinz et al. | |
| 7,840,272 B2 | 11/2010 | Kronberg et al. | |
| 7,909,983 B2 | 3/2011 | Popovich et al. | |
| 7,971,482 B2 | 7/2011 | Isogai et al. | |
| 8,016,991 B2 | 9/2011 | Scheying et al. | |
| 8,436,621 B2 | 5/2013 | Lee et al. | |
| 2001/0024729 A1 | 9/2001 | Heimann et al. | |
| 2002/0027085 A1 | 3/2002 | Stori et al. | |
| 2006/0289833 A1 | 12/2006 | Witteler et al. | |
| 2009/0211924 A1 | 8/2009 | West et al. | |
| 2010/0088995 A1 | 4/2010 | Murayama et al. | |
| 2010/0263462 A1 | 10/2010 | Nakamura | |
| 2011/0036913 A1 | 2/2011 | Merz et al. | |
| 2011/0115613 A1 | 5/2011 | Kaga et al. | |
| 2011/0140703 A1 | 6/2011 | Chiao et al. | |
| 2013/0106447 A1 | 5/2013 | Bridges et al. | |

FOREIGN PATENT DOCUMENTS

| | | |
|---|---|---|
| JP | 11-153568 A | 6/1999 |
| JP | 2929270 B2 | 8/1999 |
| JP | 2008-128734 A | 6/2008 |

* cited by examiner

CORROSION DETECTION SENSOR DEVICE

CROSS-REFERENCE TO RELATED APPLICATIONS

This is a continuation application of U.S. patent application Ser. No. 13/426,938 filed on Mar. 22, 2012, now U.S. Pat. No. 8,937,476. This application claims priority to Japanese Patent Application No. 2011-062764 filed on Mar. 22, 2011. The entire disclosures of U.S. patent application Ser. No. 13/426,938 and Japanese Patent Application No. 2011-062764 are hereby incorporated herein by reference.

BACKGROUND

1. Technical Field

The present invention relates to a corrosion detection sensor device.

2. Related Art

There are known sensor devices which, for example, measure the state of corrosion of a reinforcing bar in concrete (e.g., Japanese Laid-Open Patent Publication No. 11-153568).

Typically, the concrete in a concrete structure immediately after construction exhibits a strong alkalinity. For this reason, the reinforcing bars in a concrete structure immediately after construction have a passivation film formed on the surface thereof and are therefore safe. However, in a concrete structure that is affected after construction by acid rain, exhaust gas, and the like, the concrete will be gradually acidified, and the reinforcing bars will therefore corrode.

In view whereof, in, for example, the sensor device according to the above mentioned publication, fine wires composed of a material homogeneous to the reinforcing bars in the concrete structure are embedded in the concrete structure, and the corrosion state of the reinforcing bars in the concrete is predicted by the detection of the presence or absence of any fine wires disconnected by corrosion.

However, in the sensor device according to the above mentioned publication, between the time when the fine wires first begin to corrode and the time when a fine wire is disconnected, it is not possible to know the state of the reinforcing bars in the concrete structure nor of the concrete (more specifically, it is not possible to know, for example, the pH, or the concentration of chloride ions). Further, the reinforcing bars in the concrete structure corrode progressively between the time when the fine wires first begin to corrode and the time when a fine wire is disconnected. For this reason, entirely avoiding corrosion to the reinforcing bars in a concrete structure has not been a possibility, and this is a problem.

SUMMARY

The sensor device according to the above mentioned publication makes it possible to know the time period when corrosion of the reinforcing bars in a concrete structure has begun, according to the timing of when a fine wire is disconnected. However, the sensor device according to above mentioned publication is problematic in that after the reinforcing bars have been constructed, it is not possible, during the period up until corrosion begins, to be aware of the state of the reinforcing bars or the concrete, which changes as time elapses.

An objective of the present invention is to provide a sensor device and a measurement method with which it is possible, after reinforcing bars have been constructed, to measure changes in the state of an object to be measured during the period up until when corrosion begins, and to use the resulting information in planning the preservation of the concrete structure.

Such an objective is achieved by the present invention described below.

A sensor device according to one aspect of the present invention includes a first electrode, a second electrode, a coating film and a functional element. The first electrode includes a first metallic material, the first metallic material being a metallic material in which either a first passivation film forms on a surface thereof or the first passivation film present on the surface thereof is lost, in association with changes in the pH of a measurement site. The second electrode includes a second metallic material different from the first metallic material, the second electrode being spaced apart from the first electrode. The first electrode and the second electrode are provided on the same plane. The coating film includes a third metallic material different from the first metallic material and from the second metallic material. The coating film covers at least one of the first electrode and the second electrode. The functional element is configured to measure a difference in electric potential between the first electrode and the second electrode that changes depending on presence or absence of each of the first passivation film and the coating film as associated with the changes in pH.

According to the sensor device having such a configuration, the difference in electric potential between the first electrode and the second electrode has sharp changes which depend on the presence or absence of each of the passivation film and the coating film, which is associated with the changes in pH of the installation environments of the first electrode and the second electrode. For this reason, it is possible to accurately detect whether or not the pH of the installation environments of the first electrode and the second electrode is at or below a set value.

In the sensor device according to the above described aspect of the present invention, preferably, the functional element is configured to detect whether or not the pH of a site to be measured of an object to be measured is at or below a set value, based on the difference in electric potential between the first electrode and the second electrode.

This make it possible to detect whether or not the pH of the installation environment of the first electrode and the second electrode is at or below a set value, based on the difference in electric potential between the first electrode and the second electrode.

In the sensor device according to the above described aspect of the present invention, preferably, the second metallic material is a metallic material in which either a second passivation film is formed on a surface thereof or the second passivation film present on the surface thereof is lost, in association with changes in the pH of the measurement site, the first metallic material forms the first passivation film when the pH becomes greater than a first pH, and the second metallic material forms the second passivation film when the pH becomes greater than a second pH, the second pH being different from the first pH.

This makes it possible to accurately and respectively detect whether or not the pH values in the environments where the first electrode has been installed and where the second electrode has been installed are the first pH or lower or are the second pH or lower.

In the sensor device according to the above described aspect of the present invention, preferably, the third metallic material dissolves when the pH becomes greater than a third pH, the third pH being different from the first pH and from the second pH.

This makes it possible to accurately and respectively detect whether or not the pH values in the environments where the first electrode has been installed and where the second electrode has been installed are the first pH or lower, are the second pH or lower, or are the third pH or higher.

In the sensor device according to the above described aspect of the present invention, preferably, the first pH is 3 to 5, and the second pH is 8 to 10.

This makes it possible to know in advance that the installation environments of the first electrode and the second electrode are approaching a neutral state from an alkaline one. In view of such facts, in a case where, for example, the sensor device is used to measure the state of concrete, it is possible to predict the neutralization of the concrete environment, and to act in advance to counter and prevent the corrosion of the reinforcing bars in the concrete. It is also possible to know that the installation environments of the first electrode and the second electrode have reached an acidic state.

In the sensor device according to the above described aspect of the present invention, preferably, the third metallic material dissolves when the pH becomes greater than a lower limit of a pH range in which the first metallic material forms the first passivation film.

This makes it possible to more reliably detect changes in the pH in the installation environments of the first electrode and the second electrode, depending on the present or absence of dissolution of the coating film.

In the sensor device according to the above described aspect of the present invention, preferably, the first metallic material is iron or an iron-based alloy.

Iron or iron-based alloys are comparatively more readily and more inexpensively procured. Further, in a case where, for example, the sensor device is used to measure the state of a concrete structure, the first metallic material can be made to be the same material as that of the reinforcing bars in the concrete structure. Having the first metallic material be the same material as that of the reinforcing bars in the concrete structure makes it possible to effectively detect the state of corrosion of the reinforcing bars in the concrete structure.

In the sensor device according to the above described aspect of the present invention, preferably, the second metallic material is iron or an iron-based alloy.

Iron or iron-based alloys are comparatively more readily and more inexpensively procured. Further, in a case where, for example, the sensor device is used to measure the state of a concrete structure, the second metallic material can be made to be the same material as that of the reinforcing bars in the concrete structure. Having the second metallic material be the same material as that of the reinforcing bars in the concrete structure makes it possible to effectively detect the state of corrosion of the reinforcing bars in the concrete structure.

In the sensor device according to the above described aspect of the present invention, preferably, the second metallic material does not form a passivation film.

This makes it possible to detect, with a greater degree of precision, the changes in the pH in the installation environments of the first electrode and the second electrode, depending on the present or absence of dissolution of the passivation film of the first metal.

In the sensor device according to the above described aspect of the present invention, preferably, the first metallic material forms the first passivation film when the pH becomes greater than a pH of 3 to 5.

This makes it possible to know that the installation environments of the first electrode and the second electrode have reached an acidic state.

In the sensor device according to the above described aspect of the present invention, preferably, the first metallic material forms the first passivation film when the pH becomes greater than a pH of 8 to 10.

This makes it possible to know in advance that the installation environments of the first electrode and the second electrode are approaching a neutral state. In view of such facts, in a case where, for example, the sensor device is used to measure the state of concrete, it is possible to be aware of the neutralization and acidification status of the concrete, and to act in advance to counter and prevent the corrosion of the reinforcing bars in the concrete.

In the sensor device according to the above described aspect of the present invention, preferably, the coating film has a first coating film covering the first electrode, and a second coating film covering the second electrode, the second coating film being spaced apart from the first coating film and including a material different from that of the first coating film.

This makes it possible to detect the mutually different timings and pH values when the first coating film and the second coating film dissolve.

In the sensor device according to the above described aspect of the present invention, preferably, the coating film covers only one of the first electrode and the second electrode.

This makes it possible to detect a single timing and pH when the coating film dissolves.

In the sensor device according to the above described aspect of the present invention, preferably, an object to be measured is concrete.

This makes it possible to detect the changes in state which accompany changes in the pH of the concrete.

A measurement method according to another aspect of the present invention includes: embedding each of the first electrode and the second electrode of the sensor device according to the above described aspect in an object to be measured; and measuring a state of the object to be measured based on the difference in electric potential between the first electrode and the second electrode.

According to such a measurement method, the difference in electric potential between the first electrode and the second electrode has sharp changes which depend on the presence or absence of the passivation film, which is associated with the changes in pH of the installation environments of the first electrode and the second electrode. For this reason, it is possible to accurately detect whether or not the pH of the installation environments of the first electrode and the second electrode is at or below a set value.

A measurement method according to another aspect of the present invention includes: embedding a first electrode and a second electrode in an object to be measured with the first electrode and the second electrode being spaced apart from each other, the first electrode including a first metallic material for forming a passivation film and a second electrode including a second metallic material different from the first metallic material, at least one of the first electrode and the second electrode being covered by a coating film including a third metallic material different from the first metallic material and from the second metallic material; and measuring a state of the object to be measured based on a difference in electric potential between the first electrode and the second electrode.

According to such a measurement method, the difference in electric potential between the first electrode and the second electrode has sharp changes which depend on the presence or absence of the passivation film, which is associated with the changes in pH of the installation environments of the first electrode and the second electrode. For this reason, it is possible to accurately detect whether or not the pH of the installation environments of the first electrode and the second electrode is at or below a set value.

BRIEF DESCRIPTION OF THE DRAWINGS

Referring now to the attached drawings which form a part of this original disclosure.

DETAILED DESCRIPTION OF EXEMPLARY EMBODIMENTS

The following is a description of preferred embodiments of the sensor device and measurement method of the present invention, with reference to the accompanying drawings.

First Embodiment

Firstly, the first embodiment of the present invention shall now be described.

Figure 1:
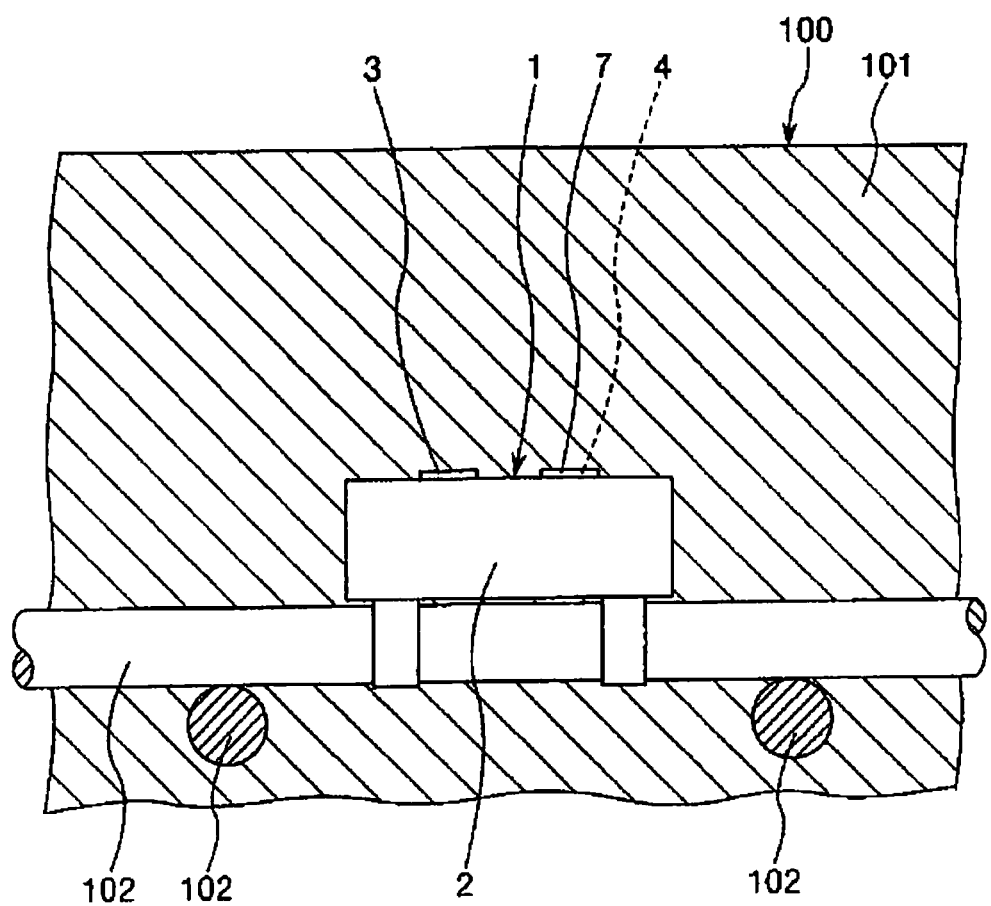
FIG. 1 is a drawing illustrating an example of the state of use of a sensor device according to a first embodiment of the present invention.
Figure 2:
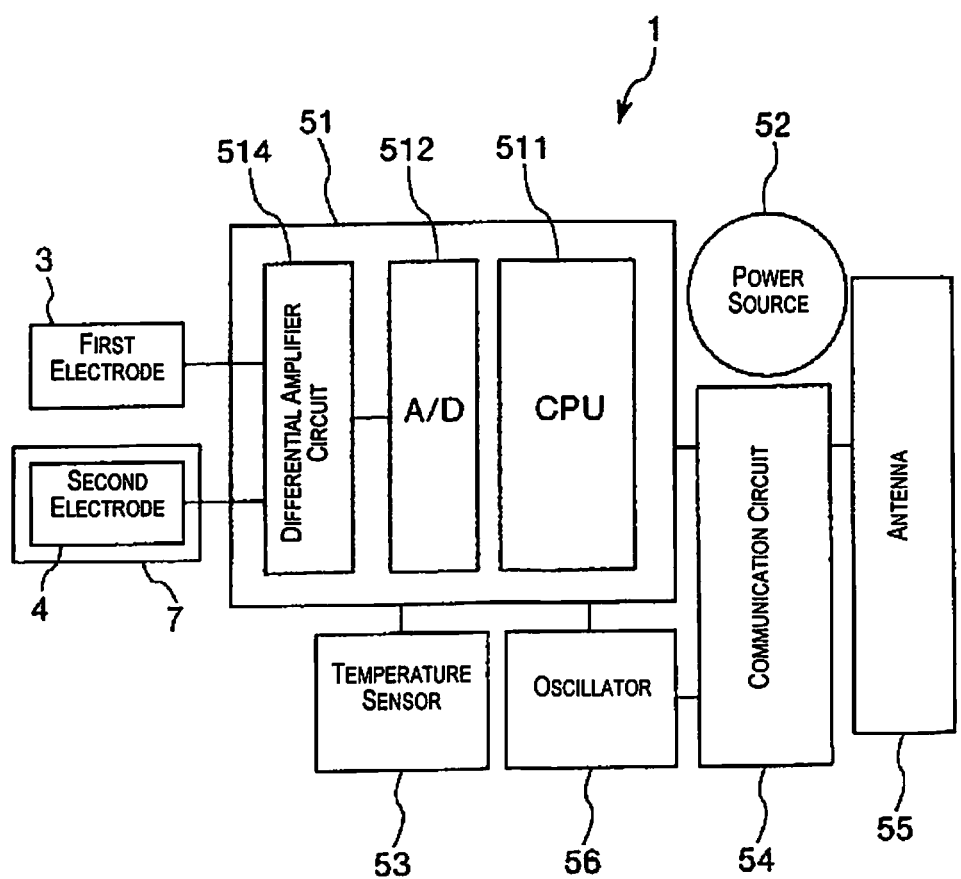
FIG. 2 is a block diagram illustrating a schematic configuration of the sensor device illustrated in FIG. 1.
Figure 3:
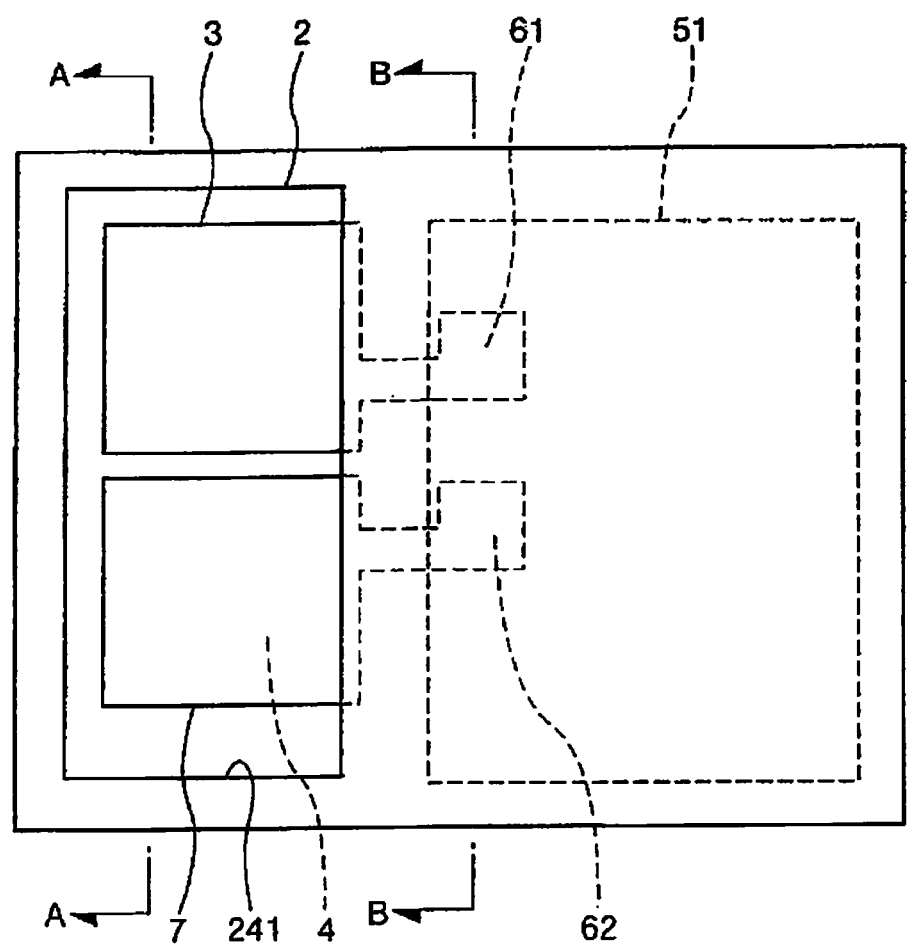
FIG. 3 is a plan view for describing a first electrode, a second electrode, and a functional element illustrated in FIG. 2.
Figure 4:
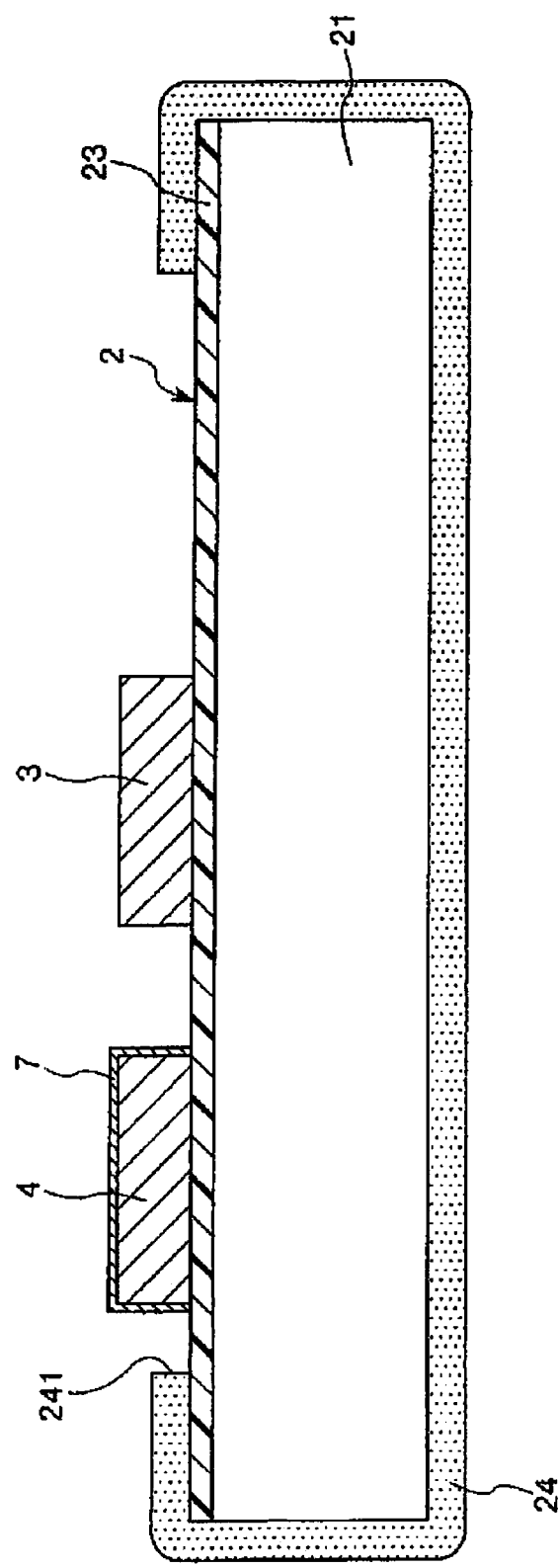
FIG. 4 is a cross-sectional view (a cross-sectional view along the A-A line in FIG. 3) for describing the first electrode and the second electrode illustrated in FIG. 2.
Figure 5:
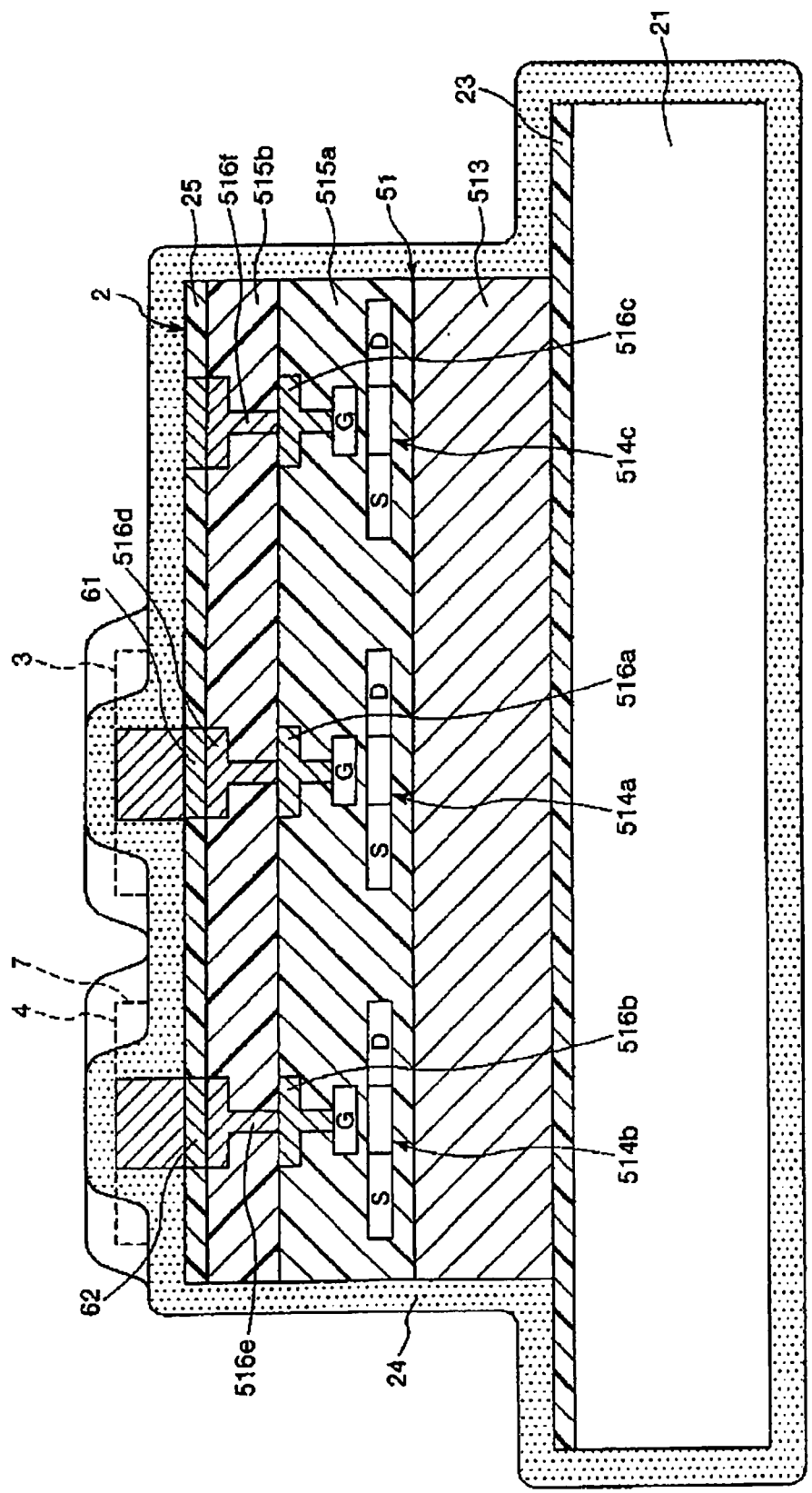
FIG. 5 is a cross-sectional view (a cross-sectional view along the B-B line in FIG. 3) for describing the functional element illustrated in FIG. 2.
Figure 6:
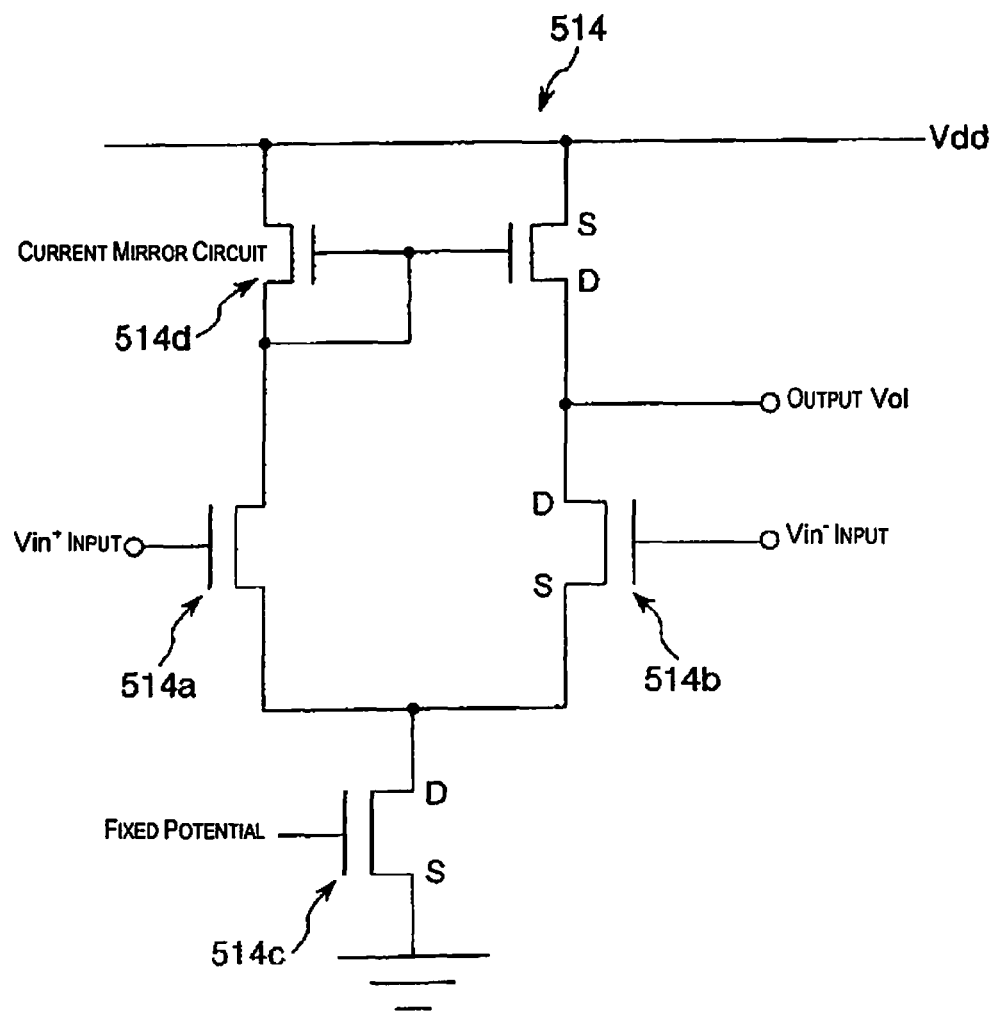
FIG. 6 is a circuit diagram illustrating a differential amplifier circuit provided to the functional element illustrated in FIG. 2.
Figure 7:
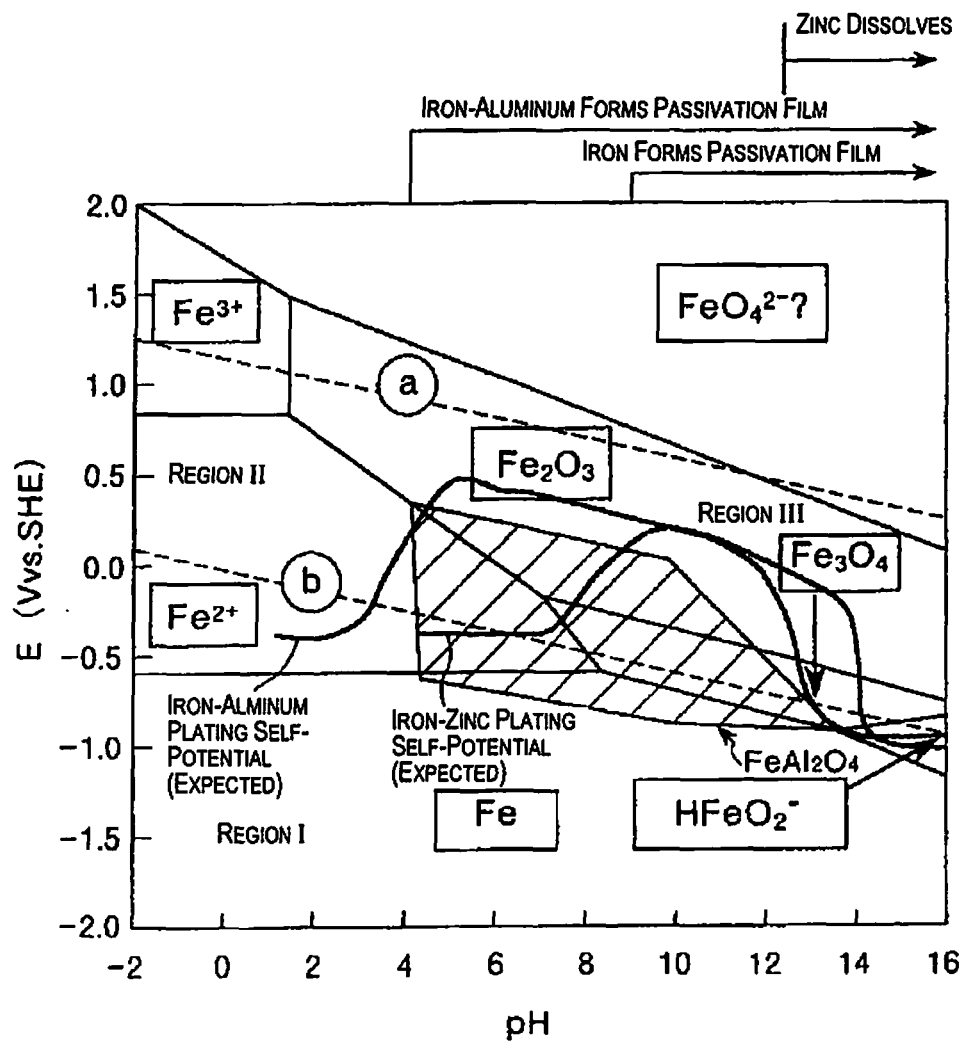
FIG. 7 is a drawing illustrating an example of the manner in which the pH and electric potential of the first electrode and the second electrode illustrated in FIG. 2 are related to the states thereof.

FIG. 1 is a drawing illustrating an example of the state of use of a sensor device according to a first embodiment of the present invention. FIG. 2 is block diagram illustrating a schematic configuration of the sensor device illustrated in FIG. 1. FIG. 3 is a plan view for describing a first electrode, a second electrode, and a functional element illustrated in FIG. 2. FIG. 4 is a cross-sectional view (a cross-sectional view along the A-A line in FIG. 3) for describing the first electrode and the second electrode illustrated in FIG. 2. FIG. 5 is a cross-sectional view (a cross-sectional view along the B-B line in FIG. 3) for describing the functional element illustrated in FIG. 2. FIG. 6 is a circuit diagram illustrating a differential amplifier circuit provided to the functional element illustrated in FIG. 2. FIG. 7 is a drawing illustrating an example of the manner in which the pH and electric potential of the first electrode and the second electrode illustrated in FIG. 2 are related to the states thereof. FIG. 8 is a drawing for describing an example of the action of the sensor device illustrated in FIG. 1.

The example described below is that of a case where the sensor device and the measurement method of the present invention are used to measure the quality of a concrete structure.

A sensor device 1 is intended to measure the quality of a concrete structure 100.

The concrete structure 100 has a plurality of reinforcing bars 102 embedded in concrete 101. The sensor device 1 is also embedded within the concrete 101 of the concrete structure 100, in the vicinity of the reinforcing bars 102. The sensor device 1 may be embedded when the concrete structure 100 is being cast, so as to be fixed to the reinforcing bars prior to the introduction of the concrete 101, or may be embedded in holes bored into the concrete 101 having hardened after casting.

The sensor device 1 has a main body 2, as well as a first electrode 3 and a second electrode 4 exposed to the surface of the main body 2. In this embodiment, the first electrode 3 and the second electrode 4 are installed so as to both be equidistant from the outer surface of the concrete structure 100. The first electrode 3 and the second electrode 4 are also installed such that the respective electrode surfaces thereof are parallel or substantially parallel to the outer surface of the concrete structure 100. The sensor device 1 is configured such that the difference in electric potential between the first electrode 3 and the second electrode 4 changes in association with changes in pH. In particular, the sensor device 1 of this embodiment has a coating film 7 for covering the second electrode 4. More detailed descriptions of the first electrode 3, the second electrode 4, and the coating film 7 shall be provided below.

The sensor device 1, as illustrated in FIG. 2, also has a functional element 51, a power source 52, a temperature sensor 53, a communication circuit 54, an antenna 55, and an oscillator 56, which are electrically connected to the first electrode 3 and to the second electrode 4 and are housed within the main body 2.

The following is a sequential description of each of the parts constituting the sensor device 1.

Main Body

The main body 2 has a function for supporting the first electrode 3, the second electrode 4, the functional element 51, and other elements.

Such a main body 2, as illustrated in FIG. 4 and FIG. 5, has a substrate 21 for supporting the first electrode 3, the second electrode 4, and the functional element 51. The substrate 21 is also intended to support the power source 52, the temperature sensor 53, the communication circuit 54, the antenna 55, and the oscillator 56, but FIGS. 3 to 5 omit a depiction of the power source 52, the temperature sensor 53, the communication circuit 54, the antenna 55, and the oscillator 56, for convenience of description.

The substrate 21 has insulating properties. Examples which can be used as the substrate 21 include, but are not particularly limited to, an alumina substrate, a resin substrate, or the like.

An insulating layer 23 constituted of an insulating resin composition, such as, for example, a solder resist, is provided on the substrate 21. The first electrode 3, the second electrode 4, and the functional element 51 are also mounted onto the substrate 21 via the insulating layer 23.

The main body 2 also has a function for housing the functional element 51, the power source 52, the temperature sensor 53, the communication circuit 54, the antenna 55, and the oscillator 56.

In particular, the main body 2 is configured so as to provide a liquid-tight housing for the functional element 51, the power source 52, the temperature sensor 53, the communication circuit 54, the antenna 55, and the oscillator 56.

Specifically, as illustrated in FIGS. 4 and 5, the main body 2 has a sealing part 24. The sealing part 24 has a function for sealing in the functional element 51, the power source 52, the temperature sensor 53, the communication circuit 54, the antenna 55, and the oscillator 56. This makes it possible to prevent the deterioration of the functional element 51, the power source 52, the temperature sensor 53, the communication circuit 54, the antenna 55, and the oscillator 56 in a case where the sensor device 1 is installed in the presence of moisture or concrete.

Herein, the sealing part 24 has an opening part 241, and is provided such that each of the parts other than the first electrode 3 and the second electrode 4 are covered, while the first electrode 3 and the second electrode 4 are exposed from the opening part 241 (see FIGS. 3 and 4). This makes it possible for the sensor device 1 to measure while the sealing part 24 prevents each of the parts other than the first electrode 3 and the second electrode 4 from deteriorating. The opening part 241 may also be formed such that at least a part or more of the first electrode 3 and at least a part or more of the second electrode 4 is exposed.

Examples of materials which can be used to constitute the sealing part 24 include: a thermoplastic resin, such as an acrylic-based resin, a urethane-based resin, or an olefin-based resin; a thermosetting resin, such as an epoxy-based resin, a melamine-based resin, or a phenol-based resin; and various other types of resin materials, it being possible to use one type thereof or a combination of two or more types thereof.

First Electrode and Second Electrode

The first electrode 3 and the second electrode 4, as illustrated in FIG. 4, are each provided on the outer surface of the main body 2 described above (more specifically, on the substrate 21). In particular, the first electrode 3 and the second electrode 4 are provided on the same plane. For this reason, it is possible to prevent the emergence of differences in the installation environments of the first electrode 3 and the second electrode 4.

The first electrode 3 and the second electrode 4 are spaced apart to such an extent (for example, several millimeters) that there is no mutual influence due to electric potential.

In this embodiment, each of the first electrode 3 and the second electrode 4 is in the form of a thin film.

The first electrode 3 is constituted of a first metallic material for forming a passivation film (which hereinafter is also simply called the "first metallic material"). In the first electrode 3 having such a configuration, a passivation film is either formed or destroyed depending on changes in the pH. In the state where the passivation film has been so formed on the first electrode 3, the electrode becomes inactive (noble) and acquires a higher self-potential (becomes more noble). In the state where the passivation film is destroyed, the first electrode is active (of low nobility). For this reason, the electric potential of the first electrode 3 has sharp changes depending on the presence or absence of the passivation film, as associated with changes in pH.

The first metallic material is not particularly limited, provided that a passivation film is formed, and examples thereof include iron, nickel, magnesium, zinc, an alloy containing these elements, or the like.

Iron forms a passivation film when the pH is greater than 9 (see FIG. 7). Iron-aluminum (0.8% Al) also forms a passivation film when the pH is greater than 4 (see FIG. 7). Nickel forms a passivation film when the pH is 8 to 14. Magnesium forms a passivation film when the pH is greater than 10.5. Zinc forms a passivation film when the pH is 6 to 12.

Of these, preferably, the first metallic material is iron or an alloy containing iron (in particular, an iron-based alloy containing 0.1 wt % to 3.5 wt % aluminum), i.e., an iron-based material (carbon steel). Iron-based materials are comparatively more readily and more inexpensively procured. In the case where, as in this embodiment, the sensor device 1 is used to measure the state of the concrete structure 100, then the first metallic material can be made to be the same material as that of the reinforcing bars 102. Having the first metallic material be the same material as that of the reinforcing bars 102 makes it possible to effectively detect the state of corrosion of the reinforcing bars 102.

On the other hand, the second electrode 4 is constituted of a second metallic material different from the first metallic material (which hereinafter is also simply called "the second metallic material"). The second electrode 4 having such a configuration does not have sharp changes in electric potential when the electric potential of the first electrode 3 changes depending on the presence or absence of the passivation film as described above. For this reason, the difference in electric potential between the first electrode 3 and the second electrode 4 has sharp changes when the electric potential of the first electrode 3 changes depending on the presence or absence of the passivation film as described above. For this reason, it is possible to accurately detect whether or not the pH values of the installation environments of the first electrode 3 and the second electrode 4 (which, in this embodiment, are in the vicinity of the reinforcing bars 102 of the concrete 101) are at or below a set value.

Provided that the second metallic material be a different metallic material from the first metallic material and be able to function as an electrode, there is no particular limitation, and various types of metallic materials can be used.

The second metallic material, with the provision of being a different metallic material from the aforesaid first metallic material, may form a passivation film or may not form a passivation film.

In a case where the second metallic material does form a passivation film, then metals which can serve as the second metallic material include those examples provided for the first metallic material.

A preferred aspect of the present invention is that a first pH and a second pH are mutually different, where the first pH (a first passivation pH) is the lower limit of the range of pH values in which the first metallic material forms a passivation film, and the second pH (a second passivation pH) is the lower limit of the range of pH values in which the second metallic material forms a passivation film. That is, the first metallic material forms a passivation film when the pH thereof becomes greater than the first pH, and the second metallic material forms a passivation film when the pH thereof becomes greater than the second pH, which is different from the first pH. This makes it possible to accurately and respectively detect whether or not the pH values in the environments where the first electrode 3 has been installed and where the second electrode 4 has been installed are the first pH or lower or are the second pH or lower.

In such a case, preferably, the first pH is 3 to 5, and the second pH is 8 to 10. This makes it possible to know in advance, by detecting whether or not the pH is at or lower than the second pH, that the installation environments of the first electrode 3 and the second electrode 4 are approaching an acidic state. In view of such facts, in a case where the sensor device 1 is used to measure the state of the concrete structure 100, as in this embodiment, it is possible to act in advance to counter and prevent the corrosion of the reinforcing bars 102. It is also possible, by detecting whether or not the pH is at or lower than the first pH, to know that the installation environments of the first electrode 3 and the second electrode 4 have reached an acidic state.

In such a case, preferably, the second metallic material is iron or an alloy containing iron (in particular, an iron-based alloy containing 0.1 wt % to 3.5 wt % aluminum), i.e., an iron-based material. Iron-based materials are comparatively more readily and more inexpensively procured. Further, in a case where the sensor device 1 is used to measure the state of the concrete structure 100, as in this embodiment, then it is possible for the second metallic material to be the same material as the reinforcing bars 102. Having the second metallic material be the same material as the reinforcing bars 102 makes it possible to effectively detect the state of corrosion of the reinforcing bars 102.

On the other hand, in a case where the second metallic material does not form a passivation film, then possible examples of the second metallic material include platinum, gold, and the like. In the case where the second metallic material does not form a passivation film, then when the installation environments of the first electrode 3 and the second electrode 4 change from a strongly alkaline state to a neutral state, the change can be accurately detected in a single stage.

In such a case, preferably, the first metallic material forms a passivation film when the pH thereof becomes greater than a pH of 3 to 5, or, greater than a pH of 8 to 10. It is possible, by detecting whether or not the pH is a pH of at or lower than a pH of 3 to 5, to know that the installation environments of the first electrode 3 and the second electrode 4 have reached an acidic state. It is also possible, by detecting whether or not the pH is at or lower than a pH of 8 to 10, to know in advance that the installation environments of the first electrode 3 and the second electrode 4 are approaching a neutral state. In view of such facts, in the case where the sensor device 1 is used to measure the state of the concrete structure 100, as in this embodiment, then it is possible to act in advance to counter and prevent the corrosion of the reinforcing bars 102.

Such a first electrode 3 and a second electrode 4 can each be formed using, for example: a chemical vapor deposition (CVD), such as plasma CVD, heat CVD, or laser CVD; vacuum deposition, sputtering (low-temperature sputtering), ion plating, or other dry plating method; electrolytic plating, immersion plating, electroless plating, or other wet plating method; or a spraying method, sol-gel method, MOD method, metal foil, or other bonding.

Coating Film

The coating film 7 is provided so as to cover the second electrode 4.

The coating film 7 is constituted of a third metallic material different from the first metallic material and from the second metallic material.

The third metallic material dissolves when the pH is higher than a predetermined pH. Thereby, in an environment at or lower than the predetermined pH, the second electrode 4 is covered by the coating film 7, and in an environment greater than the predetermined pH, the coating film 7 dissolves and is lost, and the second electrode 4 is exposed to the outside of the sensor device 1.

The third metallic material is different from the second metallic material; therefore, in the state where the second electrode 4 is covered by the coating film 7, the coating film 7 dissolves and the electric potential becomes less noble (drops) in an environment greater than the predetermined pH. In a state where the coating film 7 has been lost, the second electrode 4 is covered by the passivation film, and the electric potential becomes more noble (increases). The electric potential of the second electrode 4 will be different between the state where the coating film 7 has dissolved and the state where the coating film 7 has been lost.

Further, at a time when the two aforesaid changes in state occur, then because the third metallic material is different from the first metallic material, the electric potential of the first electrode can achieve stability.

In view of such facts, the difference in electric potential between the first electrode 3 and the second electrode 4 has sharp changes depending on the presence or absence of dissolution of the coating film 7 in association with a change in pH. For this reason, the presence or absence of the coating film 7, too, makes it possible to accurately detect whether or not the pH values of the installation environments of the first electrode 3 and the second electrode 4 are at or above a set value.

In this embodiment, because the coating film 7 covers only the second electrode 4, a single timing and pH when the coating film 7 dissolves can be detected. When the coating film 7 is made to cover only the first electrode 3, too, the single timing and pH when the coating film 7 dissolves can be detected.

Provided that the third metallic material be a different metallic material from the first metallic material and from the second metallic material and dissolve within a predetermined range of pH values, there is no particular limitation, and examples thereof include zinc, aluminum, an alloy containing these elements, or the like.

Preferably, the third metallic material dissolves when the pH becomes greater than the lower limit of the range of pH values where the aforesaid first metallic material forms the passivation film. This makes it possible to detect, with a higher degree of precision, a change in the pH values of the installation environments of the first electrode 3 and the second electrode 4, depending on the presence or absence of the coating film 7.

As a more specific example, in a case where the first metallic material and the second metallic material are each metallic materials which form a passivation film, then the third metallic material preferably dissolves when the pH reaches a third pH greater than the aforesaid first pH and the second pH. This makes it possible to accurately and respectively detect whether or not the pH values in the environments where the first electrode 3 has been installed and where the second electrode 4 has been installed are the first pH or lower, are the second pH or lower, or are the third pH or higher.

Also, preferably, the third metallic material dissolves at a pH of 7 or higher. Preferably, the third metallic material dissolves when the pH is greater than 8 (for example, aluminum), or, dissolves when the pH is greater than 10 (for example, zinc). In the case where the third metallic material dissolves when the pH is greater than 8, then it is possible to detect whether or not the environments where the first electrode 3 has been installed and where the second electrode 4 has been installed have attained a weak alkalinity. Further, in the case where the third metallic material dissolves when the pH is greater than 10, then it is possible to detect whether or not the environments where the first electrode 3 has been installed and where the second electrode 4 has been installed have attained a strong alkalinity.

Such a coating film 7 can each be formed using, for example: a chemical vapor deposition (CVD), such as plasma CVD, heat CVD, or laser CVD; vacuum deposition, sputtering (low-temperature sputtering), ion plating, or other dry plating method; electrolytic plating, immersion plating, electroless plating, or other wet plating method; or a spraying method, sol-gel method, MOD method, metal foil, or other bonding.

Functional Element

The functional element 51 is embedded in the interior of the aforesaid main body 2. The surface of the substrate 21 of the main body 2 to which the functional element 51 is provided may be identical to or opposite from that of the first electrode 3 and the second electrode 4.

The functional element 51 has a function for measuring the difference in electric potential between the first electrode 3 and the second electrode 4. This makes it possible to detect whether or not the pH values of the installation environments of the first electrode 3 and the second electrode 4 are at or below a set value, based on the difference in electric potential between the first electrode 3 and the second electrode 4.

The functional element 51 also has a function for detecting whether or not the pH of a site to be measured of the concrete structure 100, which is the object to be measured, is at or below a set value, based on the difference in electric potential between the first electrode 3 and the second electrode 4. This makes it possible to detect changes in the state of the concrete structure 100, which are associated with changes in the pH thereof.

Such a functional element 51 is, for example, an integrated circuit. More specifically, the functional element 51 is, for example, an MCU (a micro control unit) and has, as illustrated in FIG. 2, a CPU 511, an A/D conversion circuit 512, and a differential amplifier circuit 514.

A more specific description shall now be provided. The functional element 51, as illustrated in FIG. 5, has: a substrate 513; a plurality of transistors 514$a$, 514$b$, 514$c$ provided on the substrate 513; interlayer insulating films 515$a$, 515$b$ for covering the transistors 514$a$, 514$b$, 514$c$; conductor parts 516$a$, 516$b$, 516$c$, 516$d$, 516$e$, 515$f$ constituting a wiring and a conductor post; a protective film 25; and conductor parts 61, 62 constituting an electrode pad.

The substrate 513 is, for example, an SOI substrate, and the CPU 511 and the A/D conversion circuit 512 are formed thereon. Using an SOI substrate as the substrate 513 makes it possible to make the transistors 514$a$ to 514$c$ into an SOI-type MOSFET.

The plurality of transistors 514$a$, 514$b$, 514$c$ are each, for example, field-effect transistors (FETs), and constitute a part of the differential amplifier circuit 514.

The differential amplifier circuit 514, as illustrated in FIG. 6, is constituted of the three transistors 514$a$ to 514$c$ as well as of a current mirror circuit 514$d$.

The conductor part 516$a$ has one end connected to a gate electrode of the transistor 514$a$, and another end connected to the aforesaid conductor part 516$d$. The conductor part 516$d$ is electrically connected to the first electrode 3 via the conductor part 61. An electrical connection is thereby formed between the first electrode 3 and the gate electrode of the transistor 514$a$. For this reason, the drain current of the transistor 514$a$ changes in accordance with changes in the electric potential of the first electrode 3.

Similarly, the conductor part 516$b$ has one end connected to a gate electrode of the transistor 514$b$, and another end connected to the aforesaid conductor part 516$e$. The conductor part 516$e$ is electrically connected to the second electrode 4 via the conductor part 62. An electrical connection is thereby formed between the second electrode 4 and the gate electrode of the transistor 514$b$. For this reason, the drain current of the transistor 514$b$ changes in accordance with changes in the electric potential of the second electrode 4.

The conductor part 516$c$ has one end connected to a gate electrode of the transistor 514$c$, and another end connected to the aforesaid conductor part 516$f$.

The functional element 51 is operated by energization from the power source 52. Provided that the power source 52 can supplied electric power capable of operating the functional element 51, there is no particular limitation, and the power source 52 may be, for example, a battery such as a button-type battery, or may be a power source using an element having a power generation function, such as a piezoelectric element.

The functional element 51 is configured so as to be able to acquire detected temperature information on the temperature sensor 53. This makes it possible also to obtain information relating to the temperature of the measurement site. The use of such information relating to the temperature makes it possible to more accurately measure the state of the measurement site, or the anticipate changes in the measurement site with a higher degree of precision.

The temperature sensor 53 has a function for detecting the temperature of the measurement site of the concrete structure 100, which is the object to be measured. Examples of temperature sensors which can be used as such a temperature sensor 53 include but are not particularly limited to a thermocouple or other various known types.

The functional element 51 also has a function for driving and controlling the communication circuit 54. For example, the functional element 51 respectively inputs, into the communication circuit 54, information relating to the difference in electric potential between the first electrode 3 and the second electrode 4 (which hereinafter is also simply called "electric potential difference information") as well as information relating to whether or not the pH of the measurement site is at or below a set value (which hereinafter is also simply called "pH information"). The functional element 51 also additionally inputs, into the communication circuit 54, information relating to the temperature detected by the temperature sensor 53 (which hereinafter is also simply called "temperature information").

The communication circuit 54 has a function for supplying power to the antenna 55 (a transmitting function). This makes it possible for the communication circuit 54 to wirelessly transmit inputted information via the antenna 55. The transmitted information is received by a receiver (reader) provided outside the concrete structure 100.

The communication circuit 54 has, for example, a transmission circuit for transmitting electromagnetic waves, a modulation circuit having a function for modulating a signal, and the like. The communication circuit 54 may also have a down converter circuit having a function for converting a signal to a lower frequency, an up converter having a function for converting a signal to a higher frequency, an amplifier circuit having a function for amplifying a signal, a receiving circuit for receiving electromagnetic waves, a demodulating circuit having a function for demodulating a signal, and the like.

The antenna 55 is constituted of, for example, a metallic material, carbon, or the like, but is not particularly limited thereto, and forms a winding wire, a thin film, or another form.

The functional element 51 is configured so as to be able to acquire a clock signal from the oscillator 56. This makes it possible to synchronize each of the circuits, or to add time information to each of the various forms of information.

The oscillator 56 is constituted of, for example, an oscillation circuit employing a crystal oscillator, but is not particularly limited thereto.

In a measurement method using the sensor device 1 configured as has been described above (an example of the measurement method of the present invention), the first electrode 3 and the second electrode 4 are each embedded in the concrete structure 100, which is the object to be measured, in a state where the second electrode 4 is covered by the coating film 7, and the state of the concrete structure 100 is measured based on the difference in electric potential between the first electrode 3 and the second electrode 4.

The following is a description of the action of the sensor device 1 using, by way of example, a case where the first electrode 3 is constituted of iron-aluminum (0.8% aluminum), the second electrode 4 is constituted of iron (carbon steel), and the coating film 7 is constituted of zinc.

Figure 8A:
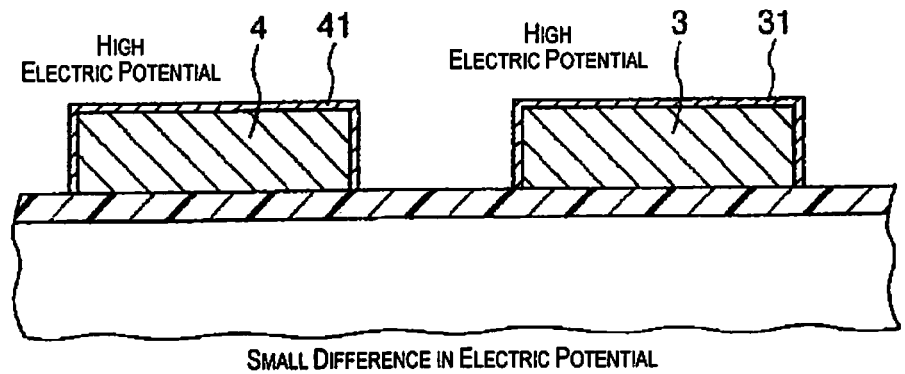
FIGS. 8A to 8C are drawings for describing an example of the action of the sensor device illustrated in FIG. 1.

In the concrete structure 100 immediately after casting, ordinarily, the concrete 101 exhibits a strong alkalinity when casting has been done appropriately. For this reason, at such a time, the coating film 7 dissolves, and the electric potential of the second electrode 4 becomes less noble (drops). As illustrated in FIG. 7, after the coating film 7 has been entirely lost, the first electrode 3 (iron-aluminum) and the second electrode 4 (iron) each form stable passivation films in the strongly alkaline environment. That is, as illustrated in FIG. 8A, a passivation film 31 is formed on the surface of the first electrode 3, and a passivation film 41 is formed on the surface of the second electrode 4. The self-potentials of the first electrode 3 and the second electrode 4 are thereby made to increase (become more noble). As a result, the difference in electric potential between the first electrode 3 and the second electrode 4 immediately after the concrete has been cast initially increases due to the dissolution of the zinc, and then is reduced after the loss of the zinc.

In a case where, for example, the concrete structure 100 is not properly cast, and the concrete 101 is neutral or exhibits weak alkalinity, the coating film 7 does not dissolve, and the difference in electric potential between the first electrode 3 and the second electrode 4 is reduced. This makes it possible to detect that the concrete structure 100 has not been properly cast. On the other hand, when the casting is done properly, the difference in electric potential increases, and then, after the loss of the coating film 7 (the zinc), the difference in electric potential is reduced.

Thereafter, the pH of the concrete 101 in the concrete structure 100 gradually changes toward becoming acidic due to the effects of carbon dioxide, acidic rain, exhaust gas, and the like.

Figure 8B:
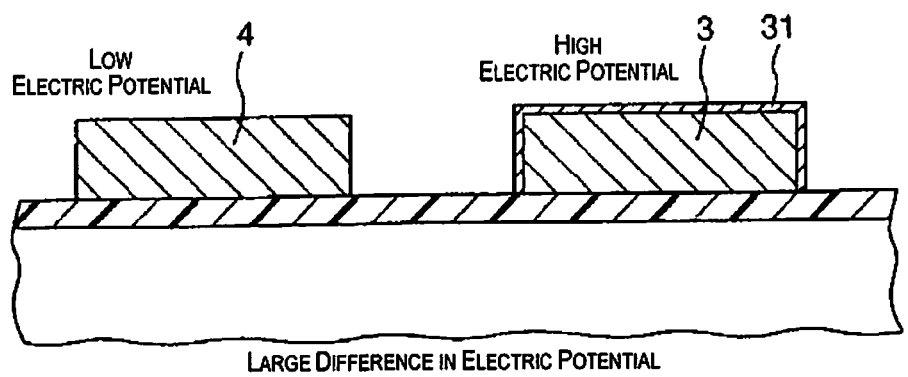

When the pH of the concrete 101 drops to as low as about 9, then, as illustrated in FIG. 8B, although the passivation film 31 of the first electrode 3 is stable and the self-potential thereof changes only slightly, the passivation film of the second electrode 4 begins to disintegrate, and thus the self-potential thereof drops (becomes less noble). The difference in electric potential between the first electrode 3 and the second electrode 4 is thereby increased.

Figure 8C:
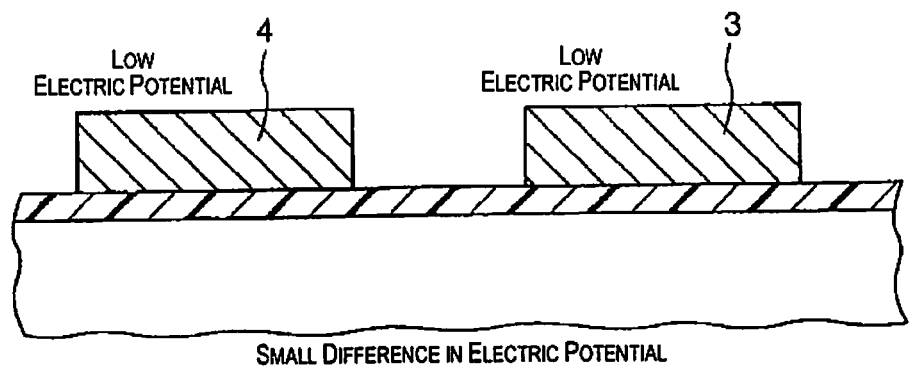

When the pH of the concrete 101 drops to as low as about 4, then, as illustrated in FIG. 8C, the passivation film of the first electrode 3 also begins to disintegrate, and the self-potential thereof drops. At such a time, because the self-potentials of both the first electrode 3 and the second electrode 4 drop together, the difference in electric potential between the first electrode 3 and the second electrode 4 is once again reduced. At such a time, each of the first electrode 3 and second electrode 4 undergoes progressive corrosion.

Thus, the difference in electric potential between the first electrode 3 and the second electrode 4 has sharp changes at three different times, which are the time when the concrete reaches strong alkalinity immediately after being cast, the time when the pH reaches about 9, and the time when the pH reaches about 4. For this reason, it is possible to detect with a high degree of precision that strong alkalinity has been reached immediately after casting, that the pH of the measurement site has reached about 9, and that the pH of the measurement site has reached about 4.

The use of such detection results makes it possible to monitor for a long time the temporal changes in the qualities of the concrete structure 100 after casting. For this reason, it is possible to become aware of the deterioration of the concrete 101 (neutralization or the intrusion of saline matter) before the reinforcing bars 102 are corroded. This makes it possible to paint the concrete structure 100 or perform repair work by a mortar compounded with an anticorrosion agent or the like, before the reinforcing bars 102 are corroded.

It is also possible to determine whether or not there has been any abnormality during the casting of the concrete structure 100. For this reason, it is possible to prevent initial difficulties with the concrete structure 100, and to improve the quality of the concrete structure 100.

According to the sensor device 1 of the first embodiment and the measurement method using the same, as has been described above, the difference in electric potential between the first electrode 3 and the second electrode 4 has sharp changes depending on the presence or absence of the passivation films and the presence or absence of the coating film 7, which are associated with changes in the pH values of the installation environments of the first electrode 3 and the second electrode 4 (i.e., the concrete 101). For this reason, it is possible to accurately detect whether or not the pH values of the installation environments of the first electrode 3 and the second electrode 4 are at or below a set value.

It is further possible to detect whether or not the pH values of the sites in the concrete structure 100, which is the object to be measured, where the first electrode 3 and the second electrode 4 have been embedded are at or below a set value, based on the difference in electric potential between the first electrode 3 and the second electrode 4. It is also possible to measure the quality of the concrete structure 100, which is the object to be measured, based on the difference in electric potential between the first electrode 3 and the second electrode 4. This makes it possible to detect changes in state of the concrete structure 100, which are associated with changes in the pH thereof.

Second Embodiment

The following is a description of a second embodiment of the present invention.

Figure 9:
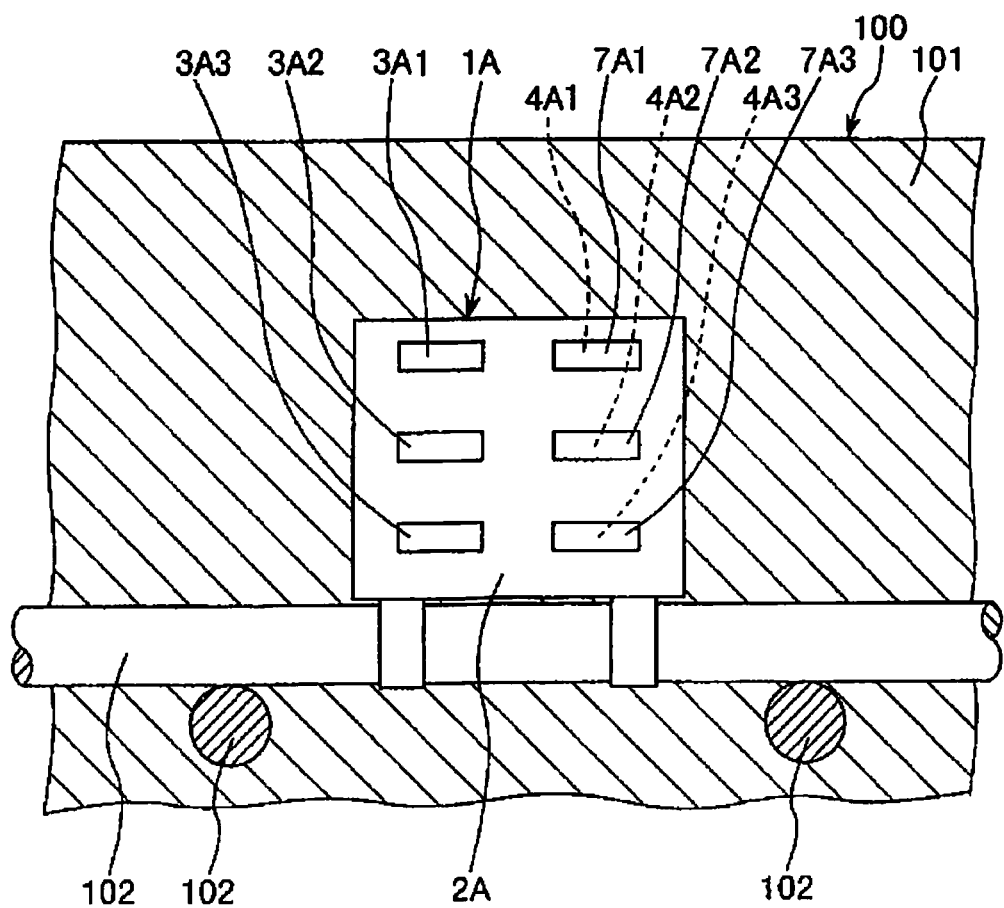
FIG. 9 is a drawing illustrating an example of the state of use of a sensor device according to a second embodiment of the present invention.

FIG. 9 is a drawing illustrating an example of the state of use of a sensor device according to the second embodiment of the present invention.

The following description of the second embodiment focuses on the points of difference with the embodiment described above, and omits a description of any similar matters.

The sensor device of the second embodiment is substantially similar to the sensor device of the first embodiment, except in that the number and shapes in plan view of the first electrode and the second electrode are different. Constituent elements which are similar to the embodiment described above have been assigned like reference numerals.

A sensor device 1A of this embodiment has: a main body 2A; a plurality of first electrodes 3A1, 3A2, 3A3 and a plurality of second electrodes 4A1, 4A2, 4A3 exposed on the surface of the main body 2A; and coating films 7A1, 7A2, 7A3 for covering the second electrodes 4A1, 4A2, 4A3.

In this embodiment, the first electrodes 3A1, 3A3, 3A3 and the second electrodes 4A1, 4A2, 4A3 are spaced mutually apart and are provided along the same surface. The first electrodes 3A1, 3A3, 3A3 and the second electrodes 4A1, 4A2, 4A3 are each installed such that the electrode surface is perpendicular to or substantially perpendicular to the outer surface of the concrete structure 100.

The plurality of first electrodes 3A1, 3A2, 3A3 are all at different distances from the outer surface of the concrete structure 100. Specifically, the plurality of first electrodes 3A1, 3A2, 3A3 are provided lined up in the stated order, from the outer surface of the concrete structure 100 inward.

Similarly, the plurality of second electrodes 4A1, 4A2, 4A3 are all at different distances from the outer surface of the concrete structure 100. Specifically, the plurality of second electrodes 4A1, 4A2, 4A3 are provided lined up in the stated order, from the outer surface of the concrete structure 100 inward.

Further, the first electrode 3A1 and the second electrode 4A1 are installed so as to both be equidistant from the outer surface of the concrete structure 100. The first electrode 3A2 and the second electrode 4A2 are installed so as to both be equidistant from the outer surface of the concrete structure 100. The first electrode 3A3 and the second electrode 4A3 are installed so as to both be equidistant from the outer surface of the concrete structure 100.

With such first electrodes 3A1, 3A2, 3A3 and second electrodes 4A1, 4A2, 4A3, the first electrodes 3A1, 3A2, 3A3 are each constituted of a first metallic material, and the second electrodes 4A1, 4A2, 4A3 are each constituted of a second metallic material. The first electrode 3A1 and the second electrode 4A1 form a pair, the first electrode 3A2 and the second electrode 4A2 form a pair, and the first electrode 3A3 and the second electrode 4A3 form a pair.

In this embodiment, the sensor device 1A is configured such that the difference in electric potential between the first electrode 3A1 and the second electrode 4A1, the difference in electric potential between the first electrode 3A2 and the second electrode 4A2, and the difference in electric potential between the first electrode 3A3 and the second electrode 4A3 can each be measured by a functional element (not shown).

The second electrode 4A1 is covered by the coating film 7A1, the second electrode 4A2 is covered by the coating film 7A2, and the second electrode 4A3 is covered by the coating film 7A3.

According to such a sensor device 1A according to the second embodiment, it is possible to accurately detect whether or not the pH values of the installation environments of the first electrode 3A1 and the second electrode 4A1, the installation environments of the first electrode 3A2 and the second electrode 4A2, and the installation environments of the first electrode 3A3 and the second electrode 4A3 are each at or below a set value. It is thus possible to accurately detect whether or not the pH values at positions of different depths from the outer surface of the concrete structure 100 are each at or below a set value. This makes it possible to detect the speed at which the pH of the concrete 101 is changing toward being more acidic. For this reason, it is possible to effective predict the neutralization and salt damage of the concrete structure 100.

Third Embodiment

The following is a description of a third embodiment of the present invention.

Figure 10:
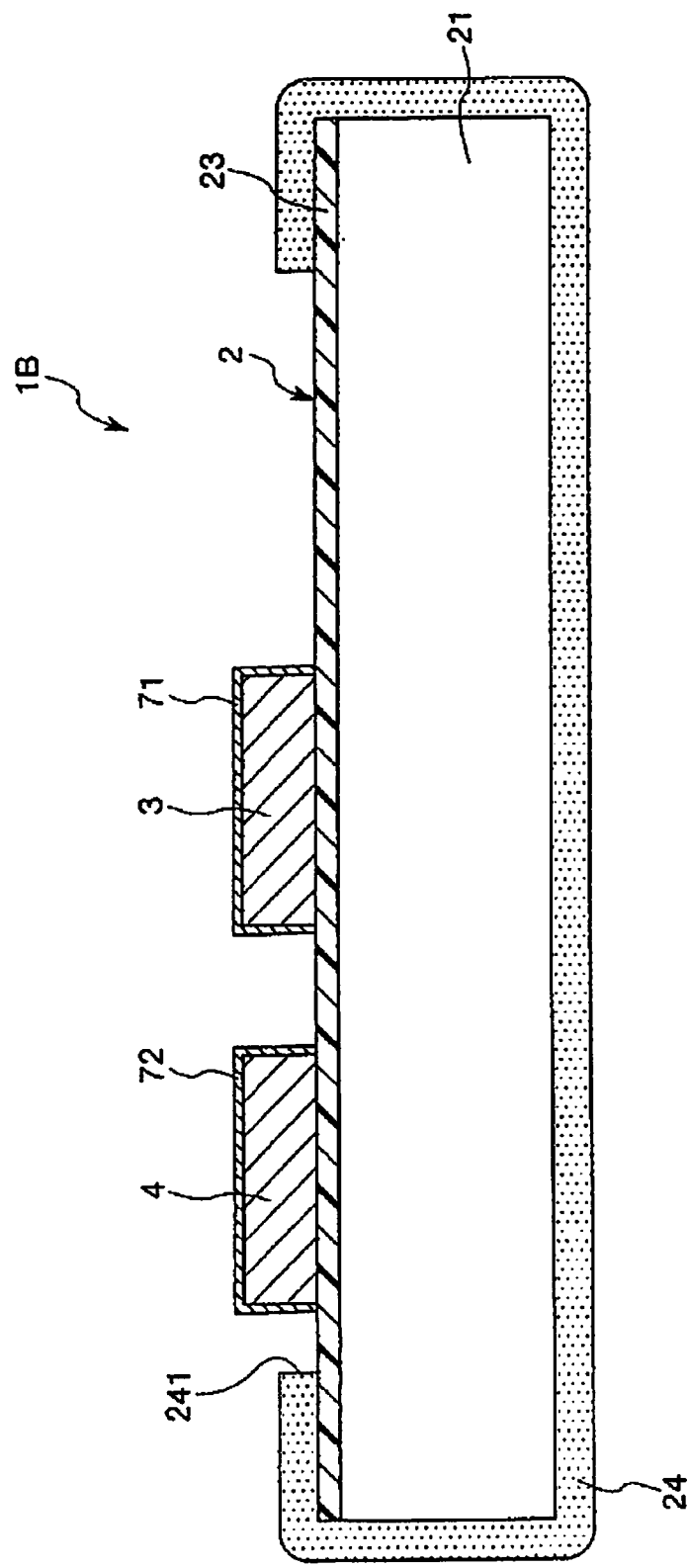
FIG. 10 is a cross-sectional view for describing a first electrode and a second electrode of a sensor device according to a third embodiment of the present invention.

FIG. 10 is a cross-sectional view for describing a first electrode and a second electrode of a sensor device according to the third embodiment of the present invention.

The following description of the third embodiment focuses on the points of difference with the embodiments described above, and omits a description of any similar matters.

The sensor device of the third embodiment is substantially similar to the sensor device of the first embodiment, except in that both the first electrode and the second electrode are covered by the coating film. Constituent elements which are similar to the embodiments described above have been assigned like reference numerals.

A sensor device 1B of this embodiment has a first coating film 71 for covering a first electrode 3, and a second coating film 72 for covering a second electrode 4.

The first coating film 71 and the second coating film 72 are provided mutually spaced apart, and are constituted of mutually different materials.

The first coating film 71 and the second coating film 72 are each constituted of third metallic materials.

Providing such a first coating film 71 and a second coating film 72 makes it possible to detect the two mutually different times and pH values at which the first coating film 71 and the second coating film 72 dissolve.

Further, preferably, the third metallic material constituting one of the coating films of the first coating film 71 and the second coating film 72 is one which dissolves when the pH is greater than 8 (for example, aluminum), and the third metallic material constituting the other coating film thereof is one which dissolves when the pH is greater than 10 (for example, zinc). This makes it possible to respectively detect whether or not the environments where the first electrode 3 has been installed and where the second electrode 4 has been installed have attained weak alkalinity and whether or not the environments are strongly alkaline.

Fourth Embodiment

The following is a description of a fourth embodiment of the present invention.

Figure 11:
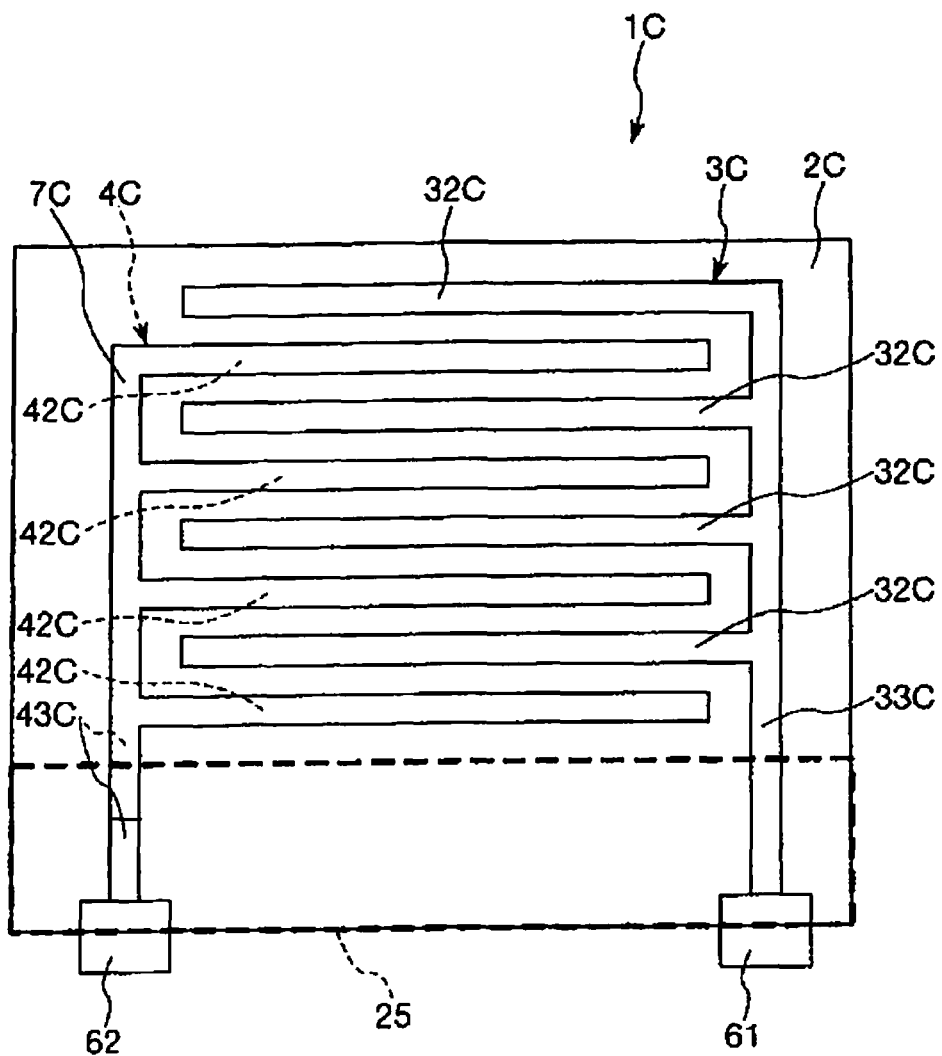
FIG. 11 is a plan view for describing a first electrode and a second electrode of a sensor device according to a fourth embodiment of the present invention.

FIG. 11 is a plan view for describing a first electrode and a second electrode of a sensor device according to the fourth embodiment of the present invention.

The following description of the fourth embodiment focuses on the points of difference with the embodiments described above, and omits a description of any similar matters.

The sensor device of the fourth embodiment is substantially similar to the sensor device of the first embodiment, except in that the shapes in plan view of the first electrode and the second electrode is different. Constituent elements which are similar to the embodiments described above have been assigned like reference numerals.

A sensor device 1C of this embodiment has: a main body 2C; a first electrode 3C and second electrode 4C exposed on the surface of the main body 2C; and a coating film 7C for covering the second electrode 4C.

The first electrode 3C has a plurality of strip-shaped parts 32C and a base part 33C, and forms the shape of a comb.

The plurality of strip-shaped parts 32C each form the shape of a strip. The plurality of strip-shaped parts 32C are provided lined up spaced mutually apart. The base part 33C links one end of each of the plurality of strip-shaped parts 32C together, and is connected to a conductor part 61.

Similarly, the second electrode 4C has a plurality of strip-shaped parts 42C and a base part 43C, and forms the shape of a comb.

The plurality of strip-shaped parts 42C each form the shape of a strip. The plurality of strip-shaped parts 42C are provided lined up spaced mutually apart. The base part 43C links one end of each of the plurality of strip-shaped parts 42C together, and is connected to a conductor part 62.

Such a first electrode 3C and a second electrode 4C are installed so as to be mutually engaged.

The plurality of strip-shaped parts 42C of the second electrode 4C are each covered by the coating film 7C, which is constituted of a third metallic material. The portion of the second electrode 4C on the side of the plurality of strip-shaped parts 42C is also covered by the coating film 7C. The end part of the base part 43C on the side of the conductor part 62 is not covered by the coating film 7C, but the portion is covered by a sealing part 25 constituted of a sealing resin.

According to the sensor device 1C having such a configuration, in a case where the first electrode 3C and the second electrode 4C are installed so as to be parallel with the outer surface of the concrete structure, then both the first electrode 3C and the second electrode 4C will be installed at environments of identical depth in the concrete, and the accuracy of the pH detection can be heightened.

The preceding is a description of the sensor device and measurement method of the present invention, based on the depicted embodiments, but the present invention is in no way limited thereto.

For example, the configuration of each of the parts in the sensor device of the present invention can be substituted with any desired configuration for exerting similar functions, and any desired configuration can be added. For example, the measurement method of the present invention may be supplemented with one or more steps of any desired objective.

Also, the embodiments described above are descriptions, by way of example, of a case where the first electrode and the second electrode are each provided on the substrate, but there is no limitation thereto, and, for example, the first electrode and the second electrode may also be provided, for example, on the outer surface of the portion of the main body of the sensor device constituted of the sealing resin.

Further, the embodiments described above are descriptions, by way of example, of a case where the first electrode and the second electrode each form the shape of a thin film, but there is no limitation thereto, and the shapes of the first electrode and the second electrode may also each form, for example, a block shape, a wire shape, or the like. In the embodiments described above, the first electrode and the second electrode are each provided along the outer surface of the main body of the sensor device, but the first electrode and the second electrode may also each be projected out from the outer surface of the main body of the sensor device.

Also, the embodiments described above are descriptions, by way of example, of a case where the functional element has a CPU, an A/D conversion circuit, and a differential amplifier circuit, but there is no limitation thereto, and, for example, a ROM, RAM, various types of drive circuits, and other, additional circuits may be incorporated into the functional element.

The embodiments described above are descriptions, by way of example, of a case where information relating to the difference in electric potential between the first electrode and the second electrode is transmitted outside the sensor device by active tag communication by wireless transmission, but there is no limitation thereto, and, for example, passive tag communication may be used to transmit the information outside the sensor device, or the information may be transmitted outside the sensor device by wire.

The embodiments described above are descriptions, by way of example, of a case where the functional element 51, the power source 52, the temperature sensor 53, the communication circuit 54, the antenna 55, and the oscillator 56 are housed in the main body 2, and these elements are, together with the first electrode 3 and the second electrode 4, embedded in the concrete structure 100, which is the object to be measured, but the functional element 51, the power source 52, the temperature sensor 53, the communication circuit 54, the antenna 55, and the oscillator 56 may also be provided outside the object to be measured.

GENERAL INTERPRETATION OF TERMS

In understanding the scope of the present invention, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Also, the terms "part," "section," "portion," "member" or "element" when used in the singular can have the dual meaning of a single part or a plurality of parts. Finally, terms of degree such as "substantially", "about" and "approximately" as used herein mean a reasonable amount of deviation of the modified term such that the end result is not significantly changed. For example, these terms can be construed as including a deviation of at least ±5% of the modified term if this deviation would not negate the meaning of the word it modifies.

While only selected embodiments have been chosen to illustrate the present invention, it will be apparent to those skilled in the art from this disclosure that various changes and modifications can be made herein without departing from the scope of the invention as defined in the appended claims. Furthermore, the foregoing descriptions of the embodiments according to the present invention are provided for illustration only, and not for the purpose of limiting the invention as defined by the appended claims and their equivalents.

What is claimed is:

1. A sensor device comprising:
a first electrode including a first metallic material, the first metallic material being a metallic material in which either a first passivation film forms on a surface thereof or the first passivation film present on the surface thereof is lost, in association with changes in the pH of a measurement site;
a second electrode including a second metallic material different from the first metallic material, the second electrode being spaced apart from the first electrode, the first electrode and the second electrode being provided on the same plane;
a coating film including a third metallic material different from the first metallic material and from the second metallic material, the coating film covering at least one of the first electrode and the second electrode; and a functional element configured to measure a difference in electric potential between the first electrode and the second electrode that changes depending on presence or absence of each of the first passivation film and the coating film in association with the changes in pH.

2. The sensor device according to claim 1, wherein the functional element is configured to detect whether or not the pH of a site to be measured of an object to be measured is at or below a set value, based on the difference in electric potential between the first electrode and the second electrode.

3. The sensor device according to claim 1, wherein the second metallic material is a metallic material in which either a second passivation film is formed on a surface thereof or the second passivation film present on the surface thereof is lost, in association with changes in the pH of the measurement site, the first metallic material forms the first passivation film when the pH becomes greater than a first pH, and the second metallic material forms the second passivation film when the pH becomes greater than a second pH, the second pH being different from the first pH.

4. The sensor device according to claim 3, wherein the third metallic material dissolves when the pH becomes greater than a third pH, the third pH being different from the first pH and from the second pH.

5. The sensor device according to claim 3, wherein the first pH is 3 to 5, and
the second pH is 8 to 10.

6. The sensor device according to claim 1, wherein the third metallic material dissolves when the pH becomes greater than a lower limit of a pH range in which the first metallic material forms the first passivation film.

7. The sensor device according to claim 1, wherein the first metallic material is iron or an iron-based alloy.

8. The sensor device according to claim 1, wherein the second metallic material is iron or an iron-based alloy.

9. The sensor device according to claim 1, wherein the second metallic material does not form a passivation film.

10. The sensor device according to claim 9, wherein the first metallic material forms the first passivation film when the pH becomes greater than a pH of 3 to 5.

11. The sensor device according to claim 9, wherein the first metallic material forms the first passivation film when the pH becomes greater than a pH of 8 to 10.

12. The sensor device according to claim 1, wherein the coating film has a first coating film covering the first electrode, and a second coating film covering the second electrode, the second coating film being spaced apart from the first coating film and including a material different from that of the first coating film.

13. The sensor device according to claim 1, wherein the coating film covers only one of the first electrode and the second electrode.

14. The sensor device according to claim 1, wherein an object to be measured by the sensor device is concrete.

15. The sensor device according to claim 1, further comprising
a sealing part defining an opening part, a part of the first electrode and a part of the second electrode being disposed in the opening part.

16. The sensor device according to claim 15, wherein the sealing part seals in the functional element, the first electrode and the second electrode such that the part of the first electrode and the part of the second electrode are exposed through the opening part.

17. The sensor device according to claim 1, wherein the first electrode is formed of a plurality of first sub electrodes, with the plurality of first sub electrodes being arranged in a first direction, the second electrode is formed of a plurality of second sub electrodes, with the plurality of second sub electrodes being arranged in a second direction, and the first direction and the second direction are parallel to each other.

18. The sensor device according to claim 1, wherein the sensor device is disposed inside a structure, the first electrode is formed of a plurality of first sub electrodes, with the plurality of first sub electrodes being arranged in a first direction, the second electrode is formed of a plurality of second sub electrodes, with the plurality of second sub electrodes being arranged in a second direction, and the first direction and the second direction are perpendicular to a surface of the structure.

19. The sensor device according to claim 18, wherein a distance from the surface of the structure to a first sub electrode, which is closest to the surface of the structure among the plurality of first sub electrodes, and a distance from the surface of the structure to a second sub electrode, which is closest to the surface of the structure among the plurality of second sub electrodes, are equal.

20. The sensor device according to claim 1, further comprising
an antenna configured to transmit measurement results measured by the functional element.

21. The sensor device according to claim 1, wherein the first electrode and the second electrode are comb-shaped.

* * * * *